United States Patent
Jimenez et al.

(10) Patent No.: US 12,263,152 B2
(45) Date of Patent: Apr. 1, 2025

(54) METHOD OF PREVENTING AND TREATING CHEMOTHERAPY-INDUCED ALOPECIA

(71) Applicant: JJR&D, LLC, Celina, TN (US)

(72) Inventors: Joaquin J. Jimenez, Miami, FL (US); John P. McCook, Frisco, TX (US)

(73) Assignee: JJR&D, LLC, Celina, TN (US)

( * ) Notice: Subject to any disclaimer, the term of this patent is extended or adjusted under 35 U.S.C. 154(b) by 0 days.

(21) Appl. No.: 18/217,172

(22) Filed: Jun. 30, 2023

(65) Prior Publication Data
US 2024/0000743 A1 Jan. 4, 2024

Related U.S. Application Data

(60) Provisional application No. 63/357,783, filed on Jul. 1, 2022.

(51) Int. Cl.
*A61K 45/06* (2006.01)
*A61K 9/00* (2006.01)
*A61K 31/327* (2006.01)
*A61P 17/14* (2006.01)

(52) U.S. Cl.
CPC .......... *A61K 31/327* (2013.01); *A61K 9/0019* (2013.01); *A61K 45/06* (2013.01); *A61P 17/14* (2018.01)

(58) Field of Classification Search
None
See application file for complete search history.

(56) References Cited

U.S. PATENT DOCUMENTS

| | | | |
|---|---|---|---|
| 5,877,209 A | 3/1999 | Yunis | |
| 6,001,378 A | 12/1999 | Desjonqueres | |
| 6,291,443 B1 * | 9/2001 | Jimenez | B82Y 5/00 514/167 |
| 7,326,420 B2 | 2/2008 | Burkhart et al. | |
| 7,682,623 B2 | 3/2010 | Eini et al. | |
| 9,901,637 B2 | 2/2018 | Jimenez et al. | |
| 10,493,103 B2 | 12/2019 | Shanler et al. | |
| 10,758,630 B2 | 9/2020 | Sample et al. | |
| 11,305,016 B2 | 4/2022 | Jimenez et al. | |
| 2003/0091602 A1 | 5/2003 | Witteler et al. | |
| 2019/0343832 A1 | 11/2019 | Laberge et al. | |
| 2021/0213021 A1 * | 7/2021 | Brichta | A61K 31/529 |
| 2022/0193383 A1 * | 6/2022 | Barman | A61K 8/69 |

FOREIGN PATENT DOCUMENTS

| | | |
|---|---|---|
| WO | WO2011032159 | 3/2011 |
| WO | WO2018105941 | 6/2018 |
| WO | WO2022035147 | 2/2022 |

OTHER PUBLICATIONS

Mayo Clinic Staff, Chemotherapy and Hair Loss: What to expect during treatment, Feb. 26, 2022 (Year: 2022).*
Itoh, Tomohiro et al., Cisplatin induces production of reative oxygen species via NADPH oxidase activation in human prostate cancer cells; Free Radical Research; Sep. 2011; 45(9): 1033-1039.
Jung, Byung-Jin et al., Dysregulation of NRF2 in Cancer: from Molecular Mechanisms to Therapeutic Opportunities; Biomolecules & Therapeutics; Dec. 7, 2017; Republic of Korea.
Zhang, Yusheng et al., Mild oxidative stress protects against chemotherapy-induced hair loss; Frontiers in Oncology; Jan. 10, 2023; Miami, Florida.
Saltsman, Jason A. et al., A Human Organoid Model of Aggressive Hepatoblastoma for Disease Modeling and Drug Testing. Cancers (Basel) . Sep. 18, 2020;12(9):2668. doi: 10.3390/cancers12092668.
Benz, Christopher C. et al., Ageing, oxidative stress and cancer: paradigms in parallax; Nat Rev Cancer; Nov. 2008; 8(11): 875-879; Novato, California.
Bao, Yi et al., Angiopoietin-like protein 3 blocks nuclear import of FAK and contributes to sorafenib response, Br J Cancer . Aug. 2018;119(4):450-461. doi: 10.1038/s41416-018-0189-4. Epub Jul. 23, 2018.
Chen, Shuo et al., Arsenic Trioxide Rescues Structural p53 Mutations through a Cryptic Allosteric Site, Cancer Cell Feb. 8, 2021;39(2):225-239.e8. doi: 10.1016/j.ccell.2020.11.013. Epub Dec. 24, 2020.
Vessey, Donald A. et al., Characterization of the oxidative stress initiated in cultured human keratinocytes by treatment with peroxides. J Invest Dermatol. 1992;99:859-63.
Rees, Matthew G. et al., Correlating chemical sensitivity and basal gene expression reveals mechanism of action, Nat Chem Biol. Feb. 2016; 12(2):109-16. doi: 10.1038/nchembio.1986. Epub Dec. 14, 2015.
Punzi, Simona et al., Development of Personalized Therapeutic Strategies by Targeting Actionable Vulnerabilities in Metastatic and Chemotherapy-Resistant Breast Cancer PDXs, Cells. Jun. 18, 2019;8(6):605. doi: 10.3390/cells8060605.
Zhang, et al., Epstein Barr virus-positive B-cell lymphoma is highly vulnerable to MDM2 inhibitors in vivo, Blood Adv. Feb. 8, 2022;6(3):891-901. doi: 10.1182/bloodadvances.2021006156.
Tobin, et al., Graying: gerontobiology of the hair follicle pigmentary unit. Exp Gerontol. 2001;36:29-54.
De Vries, Gerda et al., Establishment and characterisation of testicular cancer patient-derived xenograft models for preclinical evaluation of novel therapeutic strategies, Sci Rep. Nov. 3, 2020;10(1):18938. doi: 10.1038/s41598-020-75518-3.
Luan, Jinwei et al., Identification of differentially expressed genes associated with the enhancement of X-ray susceptibility by RITA in a hypopharyngeal squamous cell carcinoma cell line (FaDu), Radiol Oncol. Feb. 22, 2016;50(2):168-74. doi: 10.1515/raon-2016-0010. eCollection Jun. 1, 2016.
Naito, A et al., Lipid peroxides induce early onset of catagen phase in murine hair cycles. Int J Mol Med. 2008;22:725-9.
Balaban Robert S., et al., Mitochondria, oxidants, and aging. Cell. 2005;120:483-95.

(Continued)

*Primary Examiner* — Celeste A Roney
(74) *Attorney, Agent, or Firm* — Scheef & Stone, LLP; Robin L. Barnes (57) ABSTRACT

Compositions and methods for treating alopecia, particularly chemotherapy-induced alopecia, using oxidizers or oxidants, pro-oxidant compounds, or activators of P53. Compositions comprising organic peroxides such as, cumene hydroperoxide, tert-Butyl hydroperoxide (t-BHP), hydrogen peroxide, benzoyl peroxide are preferred. Compositions may be applied subcutaneously, percutaneously, or topically. Most preferably, the compositions are applied to a treatment area prior to a round of chemotherapy to prevent or reduce hair loss in the treatment area.

20 Claims, 2 Drawing Sheets

(56) References Cited

OTHER PUBLICATIONS

Aberuyi, N., et al. Negative value of CD10 -/CD34 - immunophenotype in pediatric leukemia and development of a related cell line model for investigating drug resistance, Clin Transl Oncol. Jan. 5, 2022. doi: 10.1007/s12094-021-02755-x. Online ahead of print.

Rees, Martin D. et al., Oxidative damage to extracellular matrix and its role in human pathologies. Free Radic Biol Med. 2008;44:1973-2001.

Tisma, Vesna et al., Oxidative stress and ferritin expression in the skin of patients with rosacea. J Am Acad Dermatol. 2009;60:270-6.

Spencer JD et al., Oxidative stress via hydrogen peroxide affects proopiomelanocortin peptides directly in the epidermis of patients with vitiligo. J Invest Dermatol. 2007;127:411-20.

Carugo, Alessandro et al., p53 Is a Master Regulator of Proteostasis in SMARCB1-Deficient Malignant Rhabdoid Tumors. Cancer Cell. Feb. 11, 2019;35(2):204-220.e9. doi: 10.1016/j.ccell.2019.01.006.

Botchkarev, V.A., et al., (2000). p53 is essential for chemotherapy-induced hair loss. Cancer research, 60(18), 5002-5006. PMID:11016618.

Piccini, I. et al., (2022). Peroxisome proliferator-activated receptor-γ signalling protects hair follicle stem cells from chemotherapy-induced apoptosis and epithelial-mesenchymal transition. British Journal of Dermatology, 186(1), 129-141. doi: 10.1111/bjd.20745. Epub Nov. 24, 2021.

Skalniak, Lukasz et al., Prolonged Idasanutlin (RG7388) Treatment Leads to the Generation of p53-Mutated Cells, Cancers (Basel). Oct. 24, 2018;10(11):396. doi: 10.3390/cancers10110396.

Hussein et al., protection from Chemotherapy-induced alopecia in a rat model, Science, vol. 249, issued Sep. 28, 1990, pp. 1564-1566 entire document.

Wood, JM et al., Senile hair graying: H2O2-mediated oxidative stress affects human hair color by blunting methionine sulfoxide repair. FASEB J. 2009;23:2065-75.

Isermann, Tamara et al., Suppression of HSF1 activity by wildtype p53 creates a driving force for p53 loss-of-heterozygosity, Nat Commun. Jun. 29, 2021;12(1):4019. doi: 10.1038/s41467-021-24064-1.

Ng, Samuel Y. et al., Targetable vulnerabilities in T- and NK-cell lymphomas identified through preclinical models, Nat Commun. May 22, 2018;9(1):2024. doi: 10.1038/s41467-018-04356-9.

Prager, Briana C. et al., The Meningioma Enhancer Landscape Delineates Novel Subgroups and Drives Druggable Dependencies. Cancer Discov. Nov. 2020;10(11):1722-1741. doi: 10.1158/2159-8290.CD-20-0160. Epub Jul. 23, 2020.

Buss, Meghan C. et al., The WIP1 oncogene promotes progression and invasion of aggressive medulloblastoma variants, Oncogene. Feb. 26, 2015;34(9):1126-40. doi: 10.1038/onc.2014.37. Epub Mar. 17, 2014.

Arck PC. et al., Towards a 'free radical theory of graying': melanocyte apoptosis in the aging human hair follicle is an indicator of oxidative stress induced tissue damage. FASEB J. 2006;20:1567-9.

Xu, Cheng et al., P53 wild-type/PPM1D mutant diffuse intrinsic pontine gliomas are sensitive to a MDM2 antagonist, Acta Neuropathol Commun. Nov. 3, 2021;9(1):178. doi: 10.1186/s40478-021-01270-y.

Kim, Jinchul et al., Wild-Type p53 Promotes Cancer Metabolic Switch by Inducing PUMA-Dependent Suppression of Oxidative Phosphorylation. Cancer Cell Feb. 11, 2019;35(2):191-203.e8. doi: 10.1016/j.ccell.2018.12.012. Epub Jan. 31, 2019.

Katsuoka, K. et al., Effects of epidermal growth factor, fibroblast growth factor, minoxidil and hydrocortisone on growth kinetics in human hair bulb papilla cells and root sheath fibroblasts cultured in vitro; 1987; 279(4):247-50.

Lacouture, M.E. et al., Breast Cancer Res Treat Feb; 186(1):107-114 2021.

Takashima, Iwao et al., Biology and Disease of Hair; Comparative Study of Hair Growth in Mammals, with Special References to Hair Grouping and Hair Cycle; and Hair Growth Rate in the Juvenile Stumptailed Macaque; Baltimore, Univ. Park Press, 1976; pp. 457-471.

Moore, G.P.M et al., J. Endocrinology; Effects of Epidermal Growth Factor on Hair Growth In the Mouse; 88:293-299, 1981.

Feldman et al., Zinc Fingers and Vitamin D Resistance, The Lancet, Mar. 4, 1989, p. 478. Molecular and Cellular Endocrinology, 72 (1990) pp. 57-62.

\* cited by examiner

Protective effect of Cumene Hydroperoxide at side of injection from Vp16 induced alopecia.

FIG. 1A

Protective effect of Cumene Hydroperoxide at side of injection from Vp16 induced alopecia.

FIG. 1B

METHOD OF PREVENTING AND TREATING CHEMOTHERAPY-INDUCED ALOPECIA

CROSS REFERENCE TO RELATED APPLICATION

This application claims the benefit of U.S. Provisional Application Ser. No. 63/357,783 filed on Jul. 1, 2022, which is incorporated herein by reference.

BACKGROUND OF THE INVENTION

1. Field of the Invention

The present invention relates, in general, to a method of preventing or treating alopecia induced by chemotherapeutic agents by using hydrogen peroxide, organic peroxides, metal peroxides, polymeric peroxides, peroxy acids or derivatives or analogs, including cumene hydroperoxide.

2. Description of Related Technology

Hair is a unique characteristic which differentiates mammals from other animals in the animal Kingdom. Interestingly, hair has no vital function in humans, yet its psychological function is extremely important. Loss of hair from the scalp can be extremely distressing, as is the growth of body or facial hair in excess.

Hair grows in three cycles: Anagen, Catagen, and Telogen.

ANAGEN: active hair growth, responsible for determining the final length of the hair. Eighty to Ninety percent of hair follicles on the typical human scalp (when not impacted by hair loss conditions) are in anagen at any one time. When the hair enters anagen phase: this is the onset of mitotic activity in epithelial cells. At the end of anagen, epithelial cell division declines and ceases and the follicle enters an involuntary phase known as catagen.

CATAGEN: when the lower part of the follicle involutes by apoptosis. The base of the follicle, together with its dermal papilla, begins to regress. Hair in this stage is referred to as "club" hair.

TELOGEN: The period between the completion of follicular regression and the onset of the next anagen phase is considered the telogen phase. The club hair is eventually shed through an active process termed exogen. Follicles may re-enter anagen prior to shedding of the club hair, so that the old hair is not shed until the follicle is well into its next growth phase.

Anagen is the growth phase and can last from 2 to 6 years. Catagen phase lasts from 1 to 2 weeks and consists of club hair transitions upwards toward the skin pore, while the dermal papilla separates from the follicle. In the telogen phase, the dermal papillae fully separate from the hair follicle. It lasts from 5 to 6 weeks, until the papillae move upward to meet the hair follicles again and the hair matrix begins to form new hair, returning to the anagen phase. It is during the anagen growth phase that the hair follicle is most susceptible to chemotherapy.

Alopecia is the partial or complete loss of hair from areas of the body where it normally grows, particularly the head. Alopecia may be caused by exposure to high levels of environmental oxidants, high levels of ultraviolet light, high oxygen tension, oxidizing chemicals present in cosmetic and pharmaceutical products. In addition, oxidants produced during cellular processes can cause cellular tissue damage. Indeed, cultured keratinocytes suffer irreversible damage with high doses of oxidants or long-term treatment. Additionally, topical application of lipid peroxides has been shown to induce apoptosis of hair follicles in adult mice. Alopecia is also a common and distressing side effect of many chemotherapeutic agents used to treat cancers and other diseases. There is currently no effective preventive measure or FDA approved therapeutic intervention for Chemotherapy-Induced Alopecia ("CIA"). As such, alopecia remains one of the most distressing side-effects of chemotherapy. Indeed, one of the most psychologically difficult aspects of coping with cancer is the alopecic effect of chemotherapy and its social stigma. In a study, thirty-five of forty-six patients receiving chemotherapy ranked alopecia as a more important side effect than vomiting. In addition, the negative psychosocial implications of CIA may have a significant impact on progression of the underlying disease (e.g., cancer) and the patient's response to therapy for that disease.

Progress has been made in the area of CIA with the advent of animal models. One of the most widely used has been the neonatal rat model. For example, in 1992 it was demonstrated that ImuVert, a biological response modifier derived from the bacterium *Serratia marcescens*, protected against cytarabine-induced alopecia but not cyclophosphamide-induced alopecia through the use of a neonatal rat model. Because Imuvert offered no protection from (CTX) Cyclophosphamide-induced alopecia or any combination, thereof, commonly used in the clinical setting, the use of Imuvert to protect from CIA was not pursued. In subsequent animal studies, similar protection from cytosine arabinoside-induced alopecia was observed with recombinant interleukin 1 β and later with epidermal growth factor (EGF) and fibroblast growth factor. As with Imuvert, IL-1b and EGF were not pursued in the clinical setting because of lack of protection from CTX-induced alopecia.

As another example, the protective role of the immunomodulator AS101 against CIA was demonstrated in studies on humans and the neonatal rat model, demonstrating the translational validity of the neonatal rat model to the human counterpart. However, when used under similar conditions none of these agents offered protection from alopecia induced by alkylating chemotherapies such as cyclophosphamide. Furthermore, in the clinic, combination regimens featuring strong alopecic chemotherapies are used. Accordingly, the neonatal rat model was adapted to study various compounds and chemotherapy regimens to provide a means to screen for protective compounds. After extensive testing it was demonstrated that topical pretreatment with the vitamin D3 metabolite 1,25-(OH)2D3 (referred to as "Calcitriol") protected rats from the most commonly used alopecic chemotherapies. Recently, Calcitriol was used in a proprietary topical formulation that completed a Phase I clinical trial. Twenty-three female patients undergoing taxane-type cancer chemotherapy in this Phase I study applied a dose-escalation regimen of 5, 10, 20, 40, 60, and 80 µg/mL of calcitriol twice daily during the trial. Alopecia of <50% from baseline was observed in 8 patients at Week 7, and, of which 2 patients continued to have <50% alopecia maintained at Week 15 of this clinical study. The maximum tolerated dose of the topical calcitriol drug product was not reached at the conclusion of the trial and the study investigators concluded that the topical calcitriol therapy represents a promising therapy and warrants further investigation in Phase 2/3 trials. The Vitamin D3 compositions and methods for preventing chemo-induced alopecia are detailed in U.S. Pat.

Nos. 9,901,637 and 11,305,016 titled "Vitamin D3 and analogs thereof for treating alopecia".

Another treatment for alopecia, but not CIA, is taught in U.S. Pat. No. 6,001,378. The '378 patent teaches the use of peroxidized lipids (such as almond, hazelnut, peanut, maize, grape seed, sesame, or safflower oils) with a biologically active organosilicon compound to treat alopecia, specifically androgenetic alopecia. The "peroxidized lipids" compounds that are combined with organosilicon compounds to treat alopecia as taught by the '378 patent are not peroxides as described in connection with the invention in this application, but are the lipid oxidation reaction products of polyunsaturated vegetable oils and peroxide or other oxidants to produce oxidized glyceryl triesters with a glyceride oxide content of 5-40%.

Another treatment for alopecia, including CIA, is disclosed in WO 2022/035147. The '147 publication teaches the oral administration of a salt of metaarsenite to prevent hair loss and promote hair growth. Another treatment that protects against alopecia, but not specifically CIA, is disclosed in U.S. Pat. No. 5,877,209. The '209 patent discloses the use of ascorbic acid, butylated hydroxytouluene, butylated hydroxyansile, or mixtures thereof to prevent alopecia. Both of these prior art references indicate peroxides would not be useful for treating or preventing alopecia. In fact, the '147 publication indicates that peroxide may be a contributing factor in hair loss and the testing described in the '209 patent used cumene peroxide to induce alopecia in the test rats, both indicating peroxide compounds would not be useful in treating or reducing alopecia.

Published application WO2018/105941 teaches the subcutaneous injection of a pegylated keratin or keratin-hyaluronic acid complex hydrogel, along with peroxides, specifically carbamide peroxide, calcium peroxide, methylhydroperoxide, ethylhydroperoxide, propylhydroperoxide, isopropyl hydroperoxide, or hydrogen peroxide for the treatment of alopecia. The '941 patent application shows testing of the keratin-hyaluronic acid-peroxide, PEG-keratin-peroxide, peroxide alone, and a no treatment control for hair growth in a rat model. The keratin-hyaluronic acid-peroxide and the pegylated-keratin-peroxide combinations show hair growth stimulation but the peroxide treatment alone is worse than the no treatment control for hair follicle formation. Although the '941 published application states that the invention can be used to prevent hair loss, there are no experiments listed to demonstrate this or how the compositions could be used to prevent chemo-induced alopecia. The tests using peroxide alone do, however, further indicated that peroxides would not be useful in treating or reducing alopecia or particularly CIA.

There is a need in the art for an improved treatment composition and method for use in treating alopecia, particularly CIA, that will work with a variety of chemotherapeutic agents and treatments, including alkylating chemotherapies such as cyclophosphamide. It has not previously been known to use hydrogen peroxide, organic peroxides, derivatives or analogs, including cumene hydroperoxide, for treatment of alopecia. In fact, the '147 publication indicates that peroxide may be a contributing factor in hair loss and the testing described in the '209 patent used cumene peroxide to induce alopecia in the test rats, both indicating peroxide compounds would not be useful for treating or preventing alopecia. However, according to preferred embodiments of the invention, use of hydrogen peroxide, organic peroxides, metal peroxides, polymeric peroxides, peroxy acids or derivatives or analogs, including cumene hydroperoxide results in such improvements, without the necessity of including complex synthesized keratin compounds.

SUMMARY OF THE INVENTION

The present invention relates to compositions and methods that use oxidizing agents or oxidants, or compounds that produce such agents when applied at or near a hair follicle, for the treatment of or protection against alopecia. According to one preferred embodiment of the invention, a treatment composition for treating or preventing or reducing alopecia, particularly CIA, comprises one or more of the following: (1) one or more oxidizing agents or oxidants; (2) one or more pro-oxidant compounds that generate endogenous or in-situ peroxides, preferably wherein the peroxides are generated at the location of application of the treatment composition; (3) one or more activators of P53; or (4) combinations thereof. According to another preferred embodiment, the treatment composition further comprises a pharmaceutically acceptable vehicle or carrier for subcutaneous, percutaneous, or topical application.

According to one preferred embodiment, the one or more oxidizing agents or oxidants comprises one or more of hydrogen peroxide, metal peroxides, polymeric peroxides, organic peroxides, peroxy acids, or derivatives or analogs thereof. Most preferably such peroxide compounds comprise one or more of t-BHP, cumene hydroperoxide, hydrogen peroxide, carbamide or urea peroxide, povidone-peroxide, silica xerogel hydrogen peroxide composites, calcium peroxide, zinc peroxide, barium peroxide, sodium peroxide, and benzoyl peroxide.

According to another preferred embodiment, the treatment composition does not include benzoyl peroxide. According to another preferred embodiment, the treatment composition does not include keratin, pegylated keratin, or keratin-hyaluronic acid, organosilicone or combinations thereof. According to another preferred embodiment, the treatment composition does not include any peroxidized lipids.

According to another preferred embodiment, the one or more pro-oxidant compounds comprise any in-situ activator of human cellular NADH oxidases and NOX gene activators, such as wherein the activation of such occurs at the site of application of the preferred treatment composition. According to another preferred embodiment, the one or more pro-oxidant compounds comprise one or more of doxorubicin or other anthracyclines, cisplatin, cyclophosphamide, bleomycin, camptothecin, vinblastine, disulfiram, chelerythine, paracetamol, or imidazo[1,2-a]pyridine derivatives. According to still another preferred embodiment, the one or more pro-oxidant compounds comprise an inhibitor of one or more of human cellular SOD genes, GPX genes, GSS gene, or NRF2 gene.

According to another preferred embodiment, the one or more activators of P53 comprises an MDM2-p53 modulator, most preferably RITA [2,5-bis(5-hydroxymethyl-2-thienyl) furan] or idasanutlin (RG-7388) or both.

According to another preferred embodiment, the vehicle or carrier in the composition comprises a topical gel, solution, cream, lotion, suspension, emulsion, or microemulsion or a sterile physiologically buffered aqueous solution for injection. According to other preferred embodiments, the composition may be formulated for delivery to a subject subcutaneously, percutaneously, or topically.

According to another preferred embodiment, a method of treating alopecia or protecting against alopecia or reducing hair loss comprises providing a composition comprising (1) one or more oxidizing agents or oxidants; (2) one or more pro-oxidant compounds that generate endogenous or in-situ peroxides; (3) one or more activators of P53; or (4) a combination thereof to a subject. According to another preferred embodiment, the providing step comprises applying the composition subcutaneously, percutaneously, or topically at or a near a treatment area on the subject and the providing step is carried out prior to the subject receiving one or more doses of a chemotherapeutic agent, such as one or more of a cell cycle specific agent, a non-cell cycle specific agent, or a combination thereof. According to other preferred embodiments, the composition(s) used in the method(s) are according to preferred embodiments of the compositions described herein.

According to other preferred embodiments, the method further comprises repeating the providing step at least once per day for a treatment period comprising at least 3 days before the subject receives one of the one or more doses of chemotherapeutic agent and more preferably before each dose of the chemotherapeutic agent if the subject will receive multiple doses over a period of time.

According to another preferred embodiment, the providing step comprises applying around 0.5 g to 5 g of the composition comprising the active agent and vehicle topically to the scalp.

According to another preferred embodiment, a method of treating alopecia or protecting against alopecia or reducing hair loss, including CIA, comprises applying a composition comprising hydrogen peroxide, metal peroxides, polymeric peroxides, or organic peroxides or derivatives or analogs thereof in a suitable pharmaceutical vehicle to a treatment area (an area of the scalp or other area where hair loss is to be prevented) either subcutaneously, percutaneously, or topically. According to another preferred embodiment, the method further comprises applying the composition at least once per day for at least 3 days. According to still another preferred embodiment, the composition is applied at least once per day for at least 7 days prior to commencing a round of treatment with a chemotherapy medication or compound. The application may be repeated for subsequent rounds of treatment with a chemotherapy medication or compound. For larger areas of scalp or hair needing treatment, multiple, spaced apart applications of the composition may be given by injection over the area according to another preferred embodiment. When topically applied, the composition may be applied over the entire treatment area. According to another preferred embodiment, the composition of the active agent and vehicle is applied at a dosage rate of around 1 to 20 mg per square centimeter of treatment area. Most preferably, the composition used in the preferred methods is one according to a preferred embodiment of the invention.

According to other preferred embodiments, the preferred compositions and methods are capable of reducing an amount of hair loss in a treatment area of a subject to which the composition is applied by an average of at least 25% compared to an amount of loss in a second area to which the composition is not applied that is similarly sized to the treatment area and on the same part of a subject's body as the treatment area, particularly in subjects who will receive one or more doses of a chemotherapeutic agent and when the composition is applied for a treatment period before each dose of the chemotherapeutic agent.

According to other preferred embodiments, the preferred compositions and methods are useful in preventing or reducing CIA when the chemotherapeutic agent comprises one or more of a cell cycle specific agent, a non-cell cycle specific agent, or a combination thereof. According to another preferred embodiment, the preferred compositions and methods are useful in preventing or reducing CIA when the chemotherapeutic agent comprises one or more Vp-16 (etoposide), a taxane, Adriamycin, Cytoxan, cytosine arabinoside, or a combination thereof.

Compositions and methods according to preferred embodiments are useful in treating or preventing alopecia, particularly CIA. The preferred compositions and methods may be used with numerous chemotherapeutic treatments, including cycle specific agents (such as cytosine arabinoside (ARA-C)) and non-cycle specific agents (such as Cytoxan), individually or in combination, as well as taxanes. Further objects and advantages of the invention will be clear from the description that follows.

BRIEF DESCRIPTION OF THE DRAWINGS

The compositions and methods of the invention are further described and explained in relation to the following FIGURES wherein.

DETAILED DESCRIPTION OF PREFERRED EMBODIMENTS

According to one preferred embodiment, a treatment composition for treating or preventing or reducing alopecia, particularly CIA, comprises one or more of the following (1) one or more oxidizing agents or oxidants; (2) one or more pro-oxidant compounds that generate endogenous or in-situ peroxides; (3) one or more activators of P53; or (4) combinations thereof. According to another preferred embodiment, the treatment composition further comprises a pharmaceutically acceptable vehicle or carrier for subcutaneous, percutaneous, or topical application. According to another preferred embodiment, the vehicle in the composition comprises a topical gel, solution, cream, lotion, suspension, emulsion, or microemulsion or a sterile physiologically buffered aqueous solution for injection.

The one or more oxidizing agents or oxidants preferably comprise one or more of hydrogen peroxide, organic peroxides, metal peroxides, polymeric peroxides, hydroperoxides, peroxy acids, or derivatives or analogs thereof. More preferably, the treatment composition comprises a hydroperoxide, most preferably cumene hydroperoxide or tert-Butyl hydroperoxide, but others may also be used. Other hydroperoxides that may be used include ethylbenzenehydroperoxide. According to other preferred embodiments, the peroxides comprise one or more of benzoyl peroxide, valproate peroxide, acetyl peroxide, formyl hydroperoxide, peroxypropionic acid, peroxybutyric acid, carbamide peroxide, calcium peroxide, sodium peroxide, barium peroxide, zinc peroxide, povidone (PVP)-peroxide, and silica gel hydroperoxide or organic peroxide composites.

According to one preferred embodiment, the treatment composition may include, or may exclude, benzoyl peroxide. According to a preferred embodiment, the treatment composition may include, but preferably does not include, keratin or hyaluronic acid, or compound of either or both. According to another preferred embodiment, the treatment composition may include, but preferably does not include, any peroxidized lipids or organosilicon compounds.

According to another preferred embodiment, a method of treating alopecia or protecting against alopecia, including CIA, comprises applying a composition comprising one or more oxidizing agents or oxidants, most preferably hydrogen peroxide or organic peroxides, polymeric peroxides, peroxyls or hydroperoxides or derivatives or analogs thereof, to a treatment area (an area of the scalp or other area where hair loss is to be prevented) either subcutaneously, percutaneously, or topically. According to another preferred embodiment, the method further comprises applying the composition to the treatment area at least once per day for at least 3 days. According to still another preferred embodiment, the composition is applied at least once per day for at least 7 days prior to commencing a round of treatment with a chemotherapy medication or compound. The application may be repeated for subsequent rounds of treatment with a chemotherapy medication or compound. For larger areas of scalp or hair needing treatment, multiple, spaced apart applications of the composition may be given by injection or applied topically over the area according to another preferred embodiment. When topically applied, the composition may be applied over the entire treatment area. According to another preferred embodiment, the composition is applied at a dosage rate of around 1 to 20 mg per square centimeter of treatment area. Most preferably, the composition used in the preferred methods is one according to a preferred embodiment of the invention.

When treated with preferred embodiments of compositions and methods of the invention, patients undergoing chemotherapy may experience hair loss rates in a treatment area that are at least 25% lower, more preferably at least 50% lower, than patients undergoing chemotherapy without a treatment according to a preferred embodiment or as compared to an untreated area.

EXAMPLES—Described in the below examples are methods for evaluating cumene hydroperoxide for efficacy in preventing CIA. The following examples are provided for illustration and are not intended to limit the scope of the disclosure.

Long Evans (LE) Rats with nursing pups were purchased from Envigo laboratories, Inc. Nursing LE rat pups were randomly assigned into a treatment group or a control group. The treatment group received subcutaneous (SC) injections in the nape of the neck of a treatment composition according to a preferred embodiment of the invention comprising the injection of 100 µl of a solution of cumene-hydroperoxide (80% concentration; Sigma-Aldrich, St. Louis MO, USA) in phosphate-buffered saline (PBS) vehicle with the cumene hydroperoxide first diluted at a concentration of 20 µl/ml in PBS (final concentration injected @ 1.8% cumene hydroperoxide). The injection is repeated once daily from day 5 to day 10 after birth. The control group received subcutaneous (SC) injections in the nape of the neck of the PBS vehicle alone, once daily from day 5 to day 10 after birth.

Starting at day 11 after birth, portions of the treatment group and control group were given one of the following chemotherapies Intraperitoneally (i.p.): (Example I) VP-16 (Sigma-Aldrich, St. Louis MO, USA), 1.5 mg/kg of rat weight, was given for three consecutive days; (Example II) Cytoxan (CTX) (Sigma-Aldrich, St. Louis MO, USA), 35 mg/kg, was given for one day only; or (Example III) a combination of CTX and Adriamycin (ADM) with CTX, 25 mg/kg, given for one day and ADM, 2.5 mg/kg, for three consecutive days beginning the day after the CTX administration. At these combination dose concentrations neither CTX nor ADM alone will produce alopecia.

In Example IV, starting at day 9 after birth, portions of the treatment group and control group were given the following chemotherapy Intraperitoneally (i.p.): Cytozar-U (ARA-C) (Sigma-Aldrich, St. Louis MO, USA), 50 mg/kg i.p., was given daily for seven days. Alopecia was recorded three days after the last injection of ARA-C.

Each experimental example used a new group of neonatal rats. Alopecia was recorded seven days after the last injection of each chemotherapy treatment example. Alopecia was recorded using the following scale. 0=No alopecia, 1+=0-25% alopecia, 2+=25-50% alopecia, 3+=50-75% alopecia, 4+=75-100% alopecia.

Example I—Protection From Vp-16 Induced Alopecia

Figure 1A:
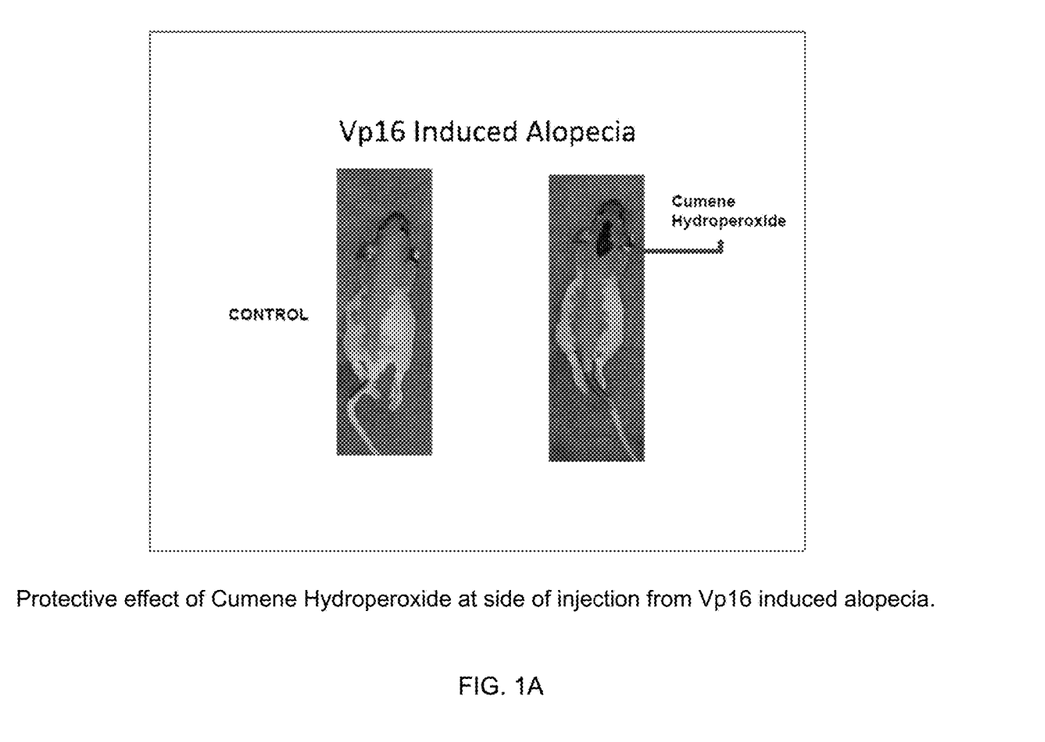
FIG. 1A is a photograph of a control rat (left) and a treated rat (right) showing a treatment according to a preferred composition and method of the invention is effective and protecting against alopecia caused by Vp-16 chemotherapy.
Figure 1B:
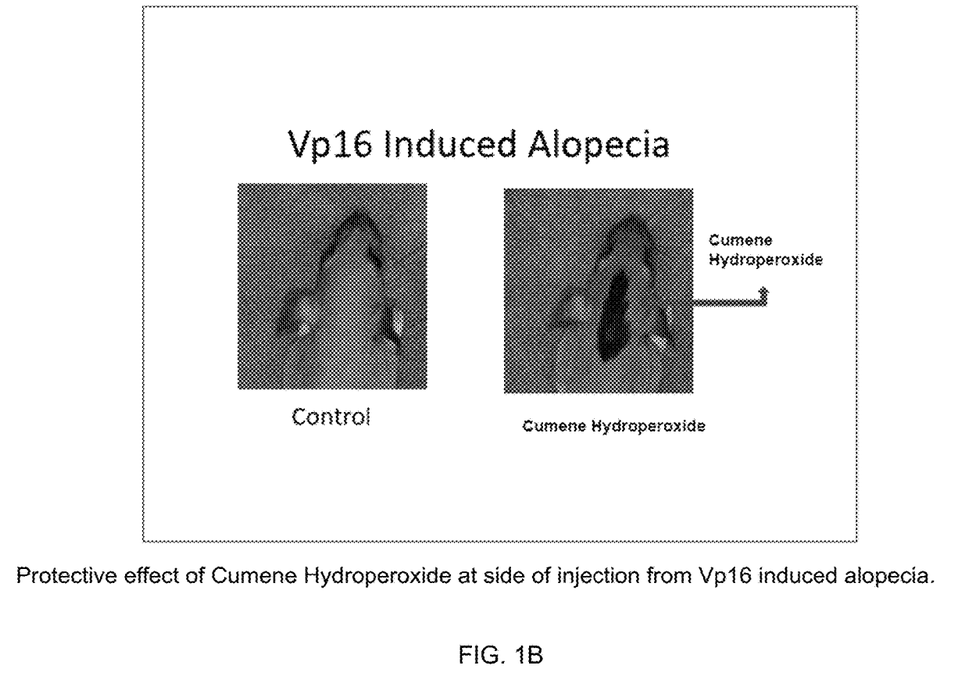
FIG. 1B is a close-up photograph of FIG. 1A.

Sixteen 5-day old rats were randomized in two groups of 8 rats each. One group of 8 rats received 100 µl of PBS SC from day 5 to day 10 after birth and served as control. The experimental treatment group of 8 rats received cumene hydroperoxide-PBS mixture (as described above) SC from day 5 to day 10. Starting on day 11, all rats received Vp-16, 1.5 mg/kg i.p. for three consecutive days. Alopecia was recorded on the seventh day from the last injection of chemotherapy (day 20 after birth). All rats in the control group became totally alopecic. In contrast, all rats in the experimental treatment group (receiving cumene hydroperoxide) were protected at the site of SC injection (Table 1) (FIGS. 1A, 1B).

TABLE 1

| GROUP | ALOPECIA | | | | |
| --- | --- | --- | --- | --- | --- |
|  | 0 | 1+ | 2+ | 3+ | 4+ |
| 1. Control | 0 | 0 | 0 | 0 | 8 |
| 2. Cumene Hydroperoxide | 8 | 0 | 0 | 0 | 0 |

Alopecia was recorded seven days after the last injection of chemothepay. Full protection from Vp-16 induced alopecia at local site of test article injection.

As can be seen from the darker spot on the treated rat on the right side of FIGS. 1A-1B, the area of SC injection of cumene hydroperoxide still has hair, indicating that the treatment aided in preventing CIA near the treatment site.

Example II—Protection From CTX Induced Alopecia

Another group of sixteen 5-day old rats were randomized in two groups of 8 rats each. One group of 8 rats received 100 µl of PBS SC from day 5 to day 10 after birth and served as control in Example II. Similarly, another group of 8 rats received cumene hydroperoxide-PBS mixture (as described above) SC from day 5 to day 10 as the treatment group. On day 11 all rats received CTX 35 mg/kg i.p. Alopecia was recorded on the seventh day from the last injection of chemotherapy. All rats in the control group became totally alopecic. In contrast, all animals in the experimental group (receiving cumene hydroperoxide) were protected at the site of SC injection (Table 2).

TABLE 2

| GROUP | ALOPECIA | | | | |
|---|---|---|---|---|---|
| | 0 | 1+ | 2+ | 3+ | 4+ |
| 1. Control | 0 | 0 | 0 | 0 | 8 |
| 2. Cumene Hydroperoxide | 8 | 0 | 0 | 0 | 0 |

Alopecia was recorded seven days after the last injection of chemothepay. Full protection from CTX induced alopecia at local site of test article injection.

Example III—Protection From CTX-ADM Induced Alopecia

Another group of sixteen 5-day old rats were randomized in two groups of 8 rats each. One group of 8 rats received 100 µl of PBS SC from day 5 to day 10 after birth and served as control for Example III. Similarly, another group of 8 rats received cumene hydroperoxide-PBS mixture (as described above) SC from day 5 to day 10 as the treatment group. On day 11 all rats received Cytoxan 25 mg/kg i.p. and Adriamycin 2.5 mg/kg i.p. once per day for three days. Alopecia was recorded on the seventh day from the last injection of chemotherapy. All rats in the control group became totally alopecic. In contrast, all animals in the experimental treatment group (receiving cumene hydroperoxide) were protected at the site of SC injection (Table 3).

TABLE 3

Table 3

| GROUP | ALOPECIA | | | | |
|---|---|---|---|---|---|
| | 0 | 1+ | 2+ | 3+ | 4+ |
| 1. Control | 0 | 0 | 0 | 0 | 8 |
| 2. Cumene Hydroperoxide | 8 | 0 | 0 | 0 | 0 |

Alopecia was recorded seven days after the last injection of chemothepay. Full protection from CTX-ADM induced alopecia at local site of test article injection.

Example IV—Protection From ARA-C Induced Alopecia

Another group of sixteen 5-day old rats were randomized in two groups of 8 rats each. One group of 8 rats received 100 µl of PBS SC from day 5 to day 10 after birth and served as control. The experimental treatment group of 8 rats received cumene hydroperoxide-PBS mixture (as described above) SC from day 5 to day 10. Starting on day 9 all rats received ARA-C 50 mg/kg i.p. daily for seven days. Alopecia was recorded on the seventh day from the last injection of chemotherapy. All rats in the control group became totally alopecic. In contrast, all rats in the experimental group (receiving cumene hydroperoxide) were protected at the site of SC injection (Table 4).

TABLE 4

Table 4

| GROUP | ALOPECIA | | | | |
|---|---|---|---|---|---|
| | 0 | 1+ | 2+ | 3+ | 4+ |
| 1. Control | 0 | 0 | 0 | 0 | 8 |
| 2. Cumene Hydroperoxide | 8 | 0 | 0 | 0 | 0 |

Alopecia was recorded three days after the last injection of chemothepay. Full protection from ARA-C induced alopecia at local site of test article injection.

The above studies show conclusively that subcutaneous dosing of a reactive oxygen species (ROS), most preferably cumene hydroperoxide (80% concentrate), at a dose of 100 µl of a 20 µl/ml dilution in PBS, dosed daily for several days prior to alopecic chemotherapy, effectively prevented chemotherapy-induced alopecia Although not shown above, other experiments on neonatal rats with cumene hydroperoxide at doses approximately 10 times or more than the concentration that showed protection from alopecia, were alopecic. Similarly, Pre-Treatment with peroxides was crucial to obtain the protective effect from CIA. For example, the use of peroxides concomitantly with chemotherapy offered no protection from CIA.

The experiments demonstrate that 1) a non-toxic/non-apoptotic concentration of an oxidizing agent in treatment compositions according to preferred embodiment can protect hair follicles from alopecia when dosing of the oxidizing agent is prior to chemotherapy and the dosing occurs locally via a subcutaneous, percutaneous, or topical dose.

For human use a topical application is preferred as multiple injections of an SC formulation are impractical and may be painful; however, an injectable formulation may also be used. One preferred composition comprises a 0.1-5% w/w peroxide concentration based on hydrogen peroxide equivalent peroxide value for an SC injectable formulation. Another preferred composition comprises a 0.5-15% w/w peroxide concentration based on hydrogen peroxide equivalent peroxide value for a topical application.

The above experiments demonstrate how the use of exogenous peroxide compounds can prevent or reduce CIA. According to another preferred embodiment, a treatment composition comprises one or more pro-oxidant compounds to prevent or reduce CIA by generating endogenous or in-situ peroxide, namely hydrogen peroxide, within or surrounding the hair follicle by topical application of one or more pro-oxidant compounds. Topical application of pro-oxidant compounds can stimulate a human biological cellular response to increase cellular and tissue hydrogen peroxide, peroxide anions or peroxyl radicals, and related reactive oxygen species. Typically, the pro-oxidant compound increases the in-situ hydrogen peroxide by activating NADPH oxidases to produce hydrogen peroxide from oxygen or by inhibiting superoxide dismutase or other antioxidant enzymes. Pro-oxidants that can be used in treatment compositions according to other preferred embodiments to prevent or reduce CIA include one or more of doxorubicin or other anthracyclines, cisplatin, bleomycin, camptothecin, vinblastine, disulfiram, cyclophosphamide, chelerythine, paracetamol, and imidazo[1,2-a]pyridine derivatives. Most preferably, these pro-oxidants would be topically applied. According to one preferred embodiment, these pro-oxidants are applied without any oxidants. According to another preferred embodiment, pro-oxidants many be applied in combination with the an oxidant, such as a peroxide.

The human cellular response to higher levels of hydrogen peroxide can also activate the p53 biological pathway which can lead to either an antioxidant or pro-oxidant apoptotic response. Since oxidative stress activates P53 it is conceivable that using activators of P53 may also be used to prevent CIA. Inhibitors of MDM2 or MDMX maintain the p53 activation towards cellular apoptosis. Without limiting the particular compounds that can be used, modulators of the MDM2-p53 or MDMX-p53 pathway can be applied topically to prevent or reduce CIA. Examples of MDM2-p53 pathway modulators that may be used in compositions according to other preferred embodiments are RITA [2,5-bis(5-hydroxymethyl-2-thienyl)furan], nutlins and idasanutlin (cis-imidazoline analogs). According to one preferred embodiment, these DM2-p53 pathway modulators are applied without any oxidants or pro-oxidants. According to another preferred embodiment, DM2-p53 pathway modulators many be applied in combination with the an oxidant, such as a peroxide, and/or a pro-oxidant.

According to still other preferred embodiments compositions for treating and/or preventing alopecia, particularly alopecia induced by one or more chemotherapeutic agents, comprise ingredients and amounts according to one or more of the following paragraphs:

(A) A composition for treating or preventing alopecia, the composition comprising; comprising (1) (a) one or more oxidizing agents or oxidants; (b) one or more pro-oxidant compounds that generate endogenous or in-situ peroxides; (c) one or more activators of P53; or (d) a combination thereof; and (2) optionally a carrier.

(B) The composition of paragraph (A) wherein the one or more oxidizing agents comprises one or more hydrogen peroxide, organic peroxides, polymeric peroxides, metal peroxides, peroxyacids, hydroperoxides, or derivatives or analogs thereof.

(C) The composition of any one of paragraphs (A)-(B) wherein the composition is configured to be applied to a treatment area subcutaneously, percutaneously, or topically.

(D) The composition of any one of paragraphs (A)-(C) wherein the one or more oxidizing agents comprises one or more of cumene hydroperoxide, tert-Butyl hydroperoxide (t-BHP), or benzoyl peroxide.

(E) The composition of any one of paragraphs (A)-(D) wherein the alopecia is induced by one or more chemotherapeutic agents comprising one or more of a cell cycle specific agent, a non-cell cycle specific agent, or a combination thereof.

(F) The composition of any one of paragraphs (A)-(E) wherein the one or more pro-oxidant compounds comprise any in-situ activator of human cellular NADH oxidases and NOX gene activators.

(G) The composition of any one of paragraphs (A)-(F) wherein the one or more pro-oxidant compounds comprise one or more of doxorubicin or other anthracyclines, cisplatin, bleomycin, camptothecin, vinblastine, disulfiram, chelerythine, cyclophosphamide, paracetamol, or imidazo[1,2-a]pyridine derivatives and wherein the composition is topically applied.

(H) The composition of any one of paragraphs (A)-(G) wherein the one or more pro-oxidant compounds comprise an inhibitor of one or more of human cellular SOD genes, GPX genes, GSS gene, or NRF2 gene.

(I) The composition of any one of paragraphs (A)-(H) wherein the one or more activators of p53 comprises an MDM2-p53 modulator.

(J) The composition of paragraph (I) wherein the MDM2-p53 modulator comprises RITA or idasanutlin or both.

(K) The composition of any one of paragraphs (A)-(J) wherein the alopecia is induced by one or more chemotherapeutic agents comprising one or more of a cell cycle specific agent, a non-cell cycle specific agent, or a combination thereof.

(L) The composition of any one of paragraphs (A)-(K) wherein the one or more chemotherapeutic agents comprise one or more of Vp-16, a taxane, Adriamycin, Cytoxan, cytosine arabinoside, or a combination thereof.

(M) The composition of any one of paragraphs (A)-(L) wherein the composition reduces an amount of hair loss in a first area to which the composition is applied by at least 25% compared to an amount of loss in a second area similarly sized to the first area to which the composition is not applied.

(N) The composition of any one of paragraphs (A)-(M) wherein the one or more chemotherapeutic agents comprise one or more of Vp-16, a taxane, Adriamycin, Cytoxan, cytosine arabinoside, or a combination thereof.

(O) The composition of paragraph (N) wherein the taxane comprises paclitaxel, docetaxel, cabezitaxel, or a combination thereof.

According to still other preferred embodiments, a method of treating or preventing alopecia, particularly alopecia induced by one or more chemotherapeutic agents, comprises steps, ingredients, and amounts according to one or more of the following paragraphs:

(P) A method for treating or preventing alopecia comprising providing a composition to a subject in need of such treatment or prevention, wherein the composition comprises: (1) one or more oxidizing agents or oxidants; (2) one or more pro-oxidant compounds that generate endogenous or in-situ peroxides; (3) one or more activators of P53; or (4) a combination thereof.

(Q) The method of paragraph (P) wherein the providing step comprises (a) applying the composition subcutaneously, percutaneously, or topically at or a near a treatment area on the subject; (b) wherein the providing step is carried out prior to the subject receiving one or more doses of the chemotherapeutic agent; and (c) wherein the chemotherapeutic agent comprises one or more of a cell cycle specific agent, a non-cell cycle specific agent, or a combination thereof.

(R) The method of any one of paragraphs (P)-(Q) wherein the one or more oxidizing agents comprises one or more of hydrogen peroxide, organic peroxides, polymeric peroxides, metal peroxides, peroxy acids, hydroperoxides, or derivatives or analogs thereof.

(S) The method of any one of paragraphs (P)-(R) wherein the one or more oxidizing agents comprises cumene hydroperoxide or benzoyl peroxide.

(T) The method of any one of paragraphs (P)-(S) wherein the composition further comprises a carrier.

(U) The method of any one of paragraphs (P)-(T) wherein the composition is subcutaneously applied at or near the treatment area.

(V) The method of any one of paragraphs (P)-(U) wherein the method reduces an amount of hair loss in the treatment area by at least 25% compared to an amount of loss in a second area of non-treatment that is similarly sized to the treatment area.

(W) The method of any one of paragraphs (P)-(V) (a) wherein the composition comprises the one or more oxidizing agents; (b) wherein the one or more oxidizing agents comprises a peroxide composition; and (c) wherein the providing step comprises applying around 0.5 to 10% by weight of the peroxide composition topically.

(X) The method of paragraph (W) wherein the peroxide composition comprises one or more of hydrogen peroxide, organic peroxides, polymeric peroxides, metal peroxides, peroxy acids, hydroperoxides, or derivatives or analogs thereof.

(Y) The method of any one of paragraphs (W)-(X) wherein the peroxide composition comprises cumene hydroperoxide.

(Z) The method of any one of paragraphs (W)-(X) wherein the peroxide composition comprises benzoyl peroxide.

(AA) The method of any one of paragraphs (P)-(Z) wherein the one or more pro-oxidant compounds comprises any in-situ activator of human cellular NADH oxidases and NOX gene activators.

(BB) The method of any one of paragraphs (P)-(AA) wherein the one or more pro-oxidant compounds comprise one or more of doxorubicin or other anthracyclines, cisplatin, bleomycin, camptothecin, cyclophosphamide, vinblastine, disulfiram, chelerythine, paracetamol, or imidazo[1,2-a]pyridine derivatives and wherein the composition is topically applied.

(CC) The method of any one of paragraphs (P)-(BB) wherein the one or more pro-oxidant compounds comprise an inhibitor of one or more of human cellular SOD genes, GPX genes, GSS gene, or NRF2 gene.

(DD) The method of any one of paragraphs (P)-(CC) wherein the one or more activators of p53 comprises an MDM2-p53 modulator.

(EE) The method of paragraph (DD) wherein the MDM2-p53 modulator comprises RITA or idasanutlin or both.

(FF) The method of any one of paragraphs (P)-(EE) further comprising repeating the providing step at least once per day for a treatment period comprising at least 7 days before the subject receives the one or more doses of the chemotherapeutic agent.

(GG) The method of any one of paragraphs (P)-(FF) wherein the subject receives multiple doses of the chemotherapeutic agent over a period of time and the method further comprises repeating the providing step at least once per day for a treatment period comprising at least 7 days before the subject receives each dose of the chemotherapeutic agent.

(HH) The method of any one of paragraphs (P)-(GG) wherein the chemotherapeutic agent comprises Vp-16, a taxane, Adriamycin, Cytoxan, cytosine arabinoside, or a combination thereof.

(II) The method of any one of paragraphs (P)-(HH) wherein the wherein the composition is according to any one of paragraphs (A)-(O).

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated.

As used herein, the terms "treat," "treating," "treatment," and the like may also include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a composition of the disclosure to an individual in need of such treatment. Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be affected over a short period, be oriented over a medium term, or can be a long-term treatment, for example within the context of a maintenance therapy. As used herein, the terms "prevent," "preventing," and "prevention," are art-recognized, and when used in relation to a condition, such as alopecia areata, is well understood in the art, and includes administration of a composition which reduces the frequency of, or delays the onset of, symptoms of a medical condition in a subject relative to a subject which does not receive the composition. Thus, prevention of alopecia includes, for example, reducing the amount of hair loss, promoting hair retention, promoting hair growth at or near treated hair follicles in a treated population versus an untreated control population, e.g., by a statistically and/or clinically significant amount.

In some cases, the compositions and methods disclosed herein comprise those for treating or preventing alopecia. In some cases, the compositions and methods disclosed herein comprise those for treating alopecia. In some cases, the compositions and methods disclosed herein comprise those for preventing alopecia.

All numerical values, ratios, or percentages indicated herein as a range include each individual amount, numerical value, or ratio within those ranges and any and all subset combinations within ranges, including subsets that overlap from one preferred range to a more preferred range. Unless specifically excluded, any preferred features and optional ingredients of any composition embodiment and/or method steps described herein may be used with any other embodiment, even if not specifically described herein with that particular embodiment. Those of ordinary skill in the art will also appreciate upon reading this specification, including the examples contained herein, that modifications and alterations to the preferred embodiments of a composition and its method of use may be made within the scope of the invention and it is intended that the scope of the invention disclosed herein be limited only by the broadest interpretation of the appended claims to which the inventor is legally entitled.

We claim:

1. A method for reducing an amount of hair loss due to alopecia induced by a chemotherapeutic agent, the method comprising the step of:

providing a composition to a subject prior to the subject receiving a dose of the chemotherapeutic agent by applying the composition subcutaneously, percutaneously, or topically at or a near a treatment area on the subject;

wherein the subject does not have alopecia at the time of the providing step;

wherein the composition comprises benzoyl peroxide in an amount sufficient to provide a 0.1% to 15% w/w peroxide concentration based on a hydrogen peroxide equivalent peroxide value; and wherein the benzoyl peroxide is the only active ingredient in the composition.

2. The method of claim 1 wherein the providing step comprises applying the composition percutaneously at or a near a treatment area on the subject; and wherein the providing step is the only step in the method for reducing alopecia induced by a chemotherapeutic agent.

3. The method of claim 1 wherein the providing step comprises applying the composition topically; and wherein the providing step is the only step in the method for reducing alopecia induced by a chemotherapeutic agent.

4. The method of claim 3 wherein the composition further comprises a carrier.

5. The method of claim 1 wherein the providing step comprises applying the composition subcutaneously; and wherein the providing step is the only step in the method for reducing alopecia induced by a chemotherapeutic agent.

6. The method of claim 3 wherein the method reduces an amount of hair loss in the treatment area by at least 25% compared to an amount of loss in a second area of non-treatment that is similarly sized to the treatment area.

7. The method of claim 6 wherein the providing step comprises applying around 0.5 to 10% by weight of the benzoyl peroxide.

8. The method of claim 6 wherein the providing step is repeated at least once per day for a treatment period comprising at least 7 days before the subject receives the dose of the chemotherapeutic agent.

9. The method of claim 6 wherein the subject receives the dose of the chemotherapeutic agent multiple times over a period of time and wherein the providing step is repeated at least once per day for a treatment period comprising at least 7 days before the subject receives each dose of the chemotherapeutic agent.

10. The method of claim 9 wherein the chemotherapeutic agent comprises Vp-16, a taxane, Adriamycin, Cytoxan, cytosine arabinoside, or a combination thereof.

11. The method of claim 5 wherein the providing step is repeated at least once per day for a treatment period comprising at least 7 days before the subject receives the dose of the chemotherapeutic agent.

12. The method of claim 5 wherein the subject receives the dose of the chemotherapeutic agent multiple times over a period of time and wherein the providing step is repeated at least once per day for a treatment period comprising at least 7 days before the subject receives each dose of the chemotherapeutic agent.

13. The method of claim 3 wherein the providing step is repeated at least once per day for a treatment period comprising at least 7 days before the subject receives the dose of the chemotherapeutic agent.

14. The method of claim 13 wherein the subject receives the dose of the chemotherapeutic agent multiple times over a period of time and wherein the providing step is repeated at least once per day for a treatment period comprising at least 7 days before the subject receives each dose of the chemotherapeutic agent.

15. A method for reducing an amount of hair loss due to alopecia induced by a chemotherapeutic agent, the method comprising the step of:
providing a composition to a subject prior to the subject receiving a dose of the chemotherapeutic agent by applying the composition subcutaneously, percutaneously, or topically at or a near a treatment area on the subject;
wherein the composition comprises benzoyl peroxide in an amount sufficient to provide a 0.1% to 15% w/w peroxide concentration based on a hydrogen peroxide equivalent peroxide value; and
wherein the benzoyl peroxide is the only active ingredient in the composition.

16. The method of claim 15 wherein the providing step is repeated at least once per day for a treatment period comprising at least 3 days before the subject receives the dose of the chemotherapeutic agent.

17. The method of claim 15 wherein the providing step is repeated at least once per day for a treatment period comprising at least 7 days before the subject receives the dose of the chemotherapeutic agent.

18. The method of claim 1 wherein the providing step is repeated at least once per day for a treatment period comprising at least 3 days before the subject receives the dose of the chemotherapeutic agent.

19. The method of claim 1 wherein the providing step is repeated at least once per day for a treatment period comprising at least 7 days before the subject receives the dose of the chemotherapeutic agent.

20. The method of claim 1 wherein the benzoyl peroxide is in an amount sufficient to provide a 0.1% to 5% w/w peroxide concentration based on a hydrogen peroxide equivalent peroxide value.

* * * * *